(12) United States Patent
Steger et al.

(10) Patent No.: US 9,277,997 B2
(45) Date of Patent: Mar. 8, 2016

(54) APPARATUS AND METHODS OF FIXATING BONE

(75) Inventors: Shon David Steger, Warsaw, IN (US); Robert Travis McKee, Jacksonville, FL (US); Shawn David Roman, Orange Park, FL (US); Bradley James Winterroth, Jacksonville, FL (US)

(73) Assignee: BIOMET MICROFIXATION, LLC, Jacksonville, FL (US)

( * ) Notice: Subject to any disclaimer, the term of this patent is extended or adjusted under 35 U.S.C. 154(b) by 237 days.

(21) Appl. No.: 13/458,401

(22) Filed: Apr. 27, 2012

(65) Prior Publication Data

US 2012/0226327 A1 Sep. 6, 2012

Related U.S. Application Data

(62) Division of application No. 12/101,571, filed on Apr. 11, 2008, now abandoned.

(51) Int. Cl.
*A61F 2/28* (2006.01)
*A61B 17/68* (2006.01)
*A61B 17/00* (2006.01)
*A61F 2/30* (2006.01)

(52) U.S. Cl.
CPC .............. *A61F 2/2846* (2013.01); *A61B 17/688* (2013.01); *A61B 2017/00004* (2013.01); *A61B 2017/00951* (2013.01); *A61F 2/2875* (2013.01); *A61F 2002/30448* (2013.01); *A61F 2220/005* (2013.01)

(58) Field of Classification Search
CPC ................ A61F 2002/3008; A61F 2002/2835; A61F 2002/30583; A61F 2210/0085; A61F 2002/30062; A61F 2002/30622; A61L 27/50
USPC .......................................... 623/17.17–17.19
See application file for complete search history.

(56) References Cited

U.S. PATENT DOCUMENTS 3,849,805 A 11/1974 Leake et al.
4,239,113 A * 12/1980 Gross et al. ................... 206/568

(Continued)

FOREIGN PATENT DOCUMENTS

JP 2001-327520 A 11/2001
WO WO 97/38676 A 10/1997

(Continued)

OTHER PUBLICATIONS

International Search Report dated Oct. 15, 2009, issued in corresponding International Application No. PCT/US2009/040094.

*Primary Examiner* — Bruce E Snow
*Assistant Examiner* — Melissa Hoban
(74) *Attorney, Agent, or Firm* — Arent Fox LLP

(57) ABSTRACT

Apparatus and methods of fixating bone include repairing or remodeling a hard tissue defect with a composite bone structure. The composite bone structure includes at least two hard tissues or bones and a scaffold material fixed together by an adhesive component. The apparatus and methods include positioning the hard tissues/bones, conforming the scaffold material to at least a portion of a surface of the hard tissues/bones, contacting the adhesive component with the hard tissues/bones and the scaffold material, and changing the material state of the adhesive component to another material state at which the adhesive component fixes together the hard tissues/bones and the scaffold material, thereby forming a composite bone structure having a desired rigidity.

23 Claims, 4 Drawing Sheets

(56) References Cited

U.S. PATENT DOCUMENTS

| | | | |
|---|---|---|---|
| 4,329,743 A | 5/1982 | Alexander et al. | |
| 4,512,038 A | 4/1985 | Alexander et al. | |
| 4,636,215 A | 1/1987 | Schwartz | |
| 4,678,436 A | 7/1987 | Kondo et al. | |
| 4,966,599 A | 10/1990 | Pollock | |
| 5,306,304 A | 4/1994 | Gendler | |
| 5,397,361 A | 3/1995 | Clark | |
| 5,413,577 A | 5/1995 | Pollock | |
| 5,461,124 A | 10/1995 | Ritter et al. | |
| 5,468,242 A | 11/1995 | Reisberg | |
| 5,496,371 A | 3/1996 | Eppley et al. | |
| 5,503,164 A | 4/1996 | Friedman | |
| 5,549,678 A | 8/1996 | Prostkoff | |
| 5,556,429 A * | 9/1996 | Felt | 128/898 |
| 5,569,250 A | 10/1996 | Sarver et al. | |
| 5,660,225 A | 8/1997 | Saffran | |
| 5,690,631 A | 11/1997 | Duncan et al. | |
| 5,766,176 A | 6/1998 | Duncan | |
| 5,773,418 A | 6/1998 | Edwardson et al. | |
| 5,839,899 A | 11/1998 | Robinson | |
| 5,868,746 A | 2/1999 | Sarver et al. | |
| 5,876,447 A | 3/1999 | Arnett | |
| 5,919,234 A | 7/1999 | Lemperle et al. | |
| 6,071,291 A | 6/2000 | Forst et al. | |
| 6,117,425 A | 9/2000 | MacPhee et al. | |
| 6,206,883 B1 | 3/2001 | Tunc | |
| 6,221,075 B1 * | 4/2001 | Tormala et al. | 606/77 |
| 6,228,117 B1 | 5/2001 | De Bruijn et al. | |
| 6,238,214 B1 | 5/2001 | Robinson | |
| 6,280,473 B1 | 8/2001 | Lemperle et al. | |
| 6,313,819 B1 | 11/2001 | Maekawa et al. | |
| 6,325,803 B1 | 12/2001 | Schumacher et al. | |
| 6,328,765 B1 | 12/2001 | Hardwick et al. | |
| 6,336,930 B1 * | 1/2002 | Stalcup et al. | 606/284 |
| 6,391,049 B1 | 5/2002 | McNally et al. | |
| 6,391,059 B1 | 5/2002 | Lemperle et al. | |
| 6,394,807 B2 | 5/2002 | Robinson | |
| 6,485,503 B2 | 11/2002 | Jacobs et al. | |
| 6,511,511 B1 | 1/2003 | Slivka et al. | |
| 6,605,090 B1 * | 8/2003 | Trieu et al. | 606/281 |
| 6,645,226 B1 | 11/2003 | Jacobs et al. | |
| 6,656,489 B1 | 12/2003 | Mahmood et al. | |
| 6,685,707 B2 | 2/2004 | Roman et al. | |
| 6,692,497 B1 | 2/2004 | Tormala et al. | |
| 6,692,498 B1 | 2/2004 | Niiranen et al. | |
| 6,696,073 B2 | 2/2004 | Boyce et al. | |
| 6,712,851 B1 | 3/2004 | Lemperle et al. | |
| 6,716,957 B2 | 4/2004 | Tunc | |
| 6,731,252 B2 | 5/2004 | Sugiyama et al. | |
| 6,827,743 B2 | 12/2004 | Eisermann et al. | |
| 6,893,452 B2 | 5/2005 | Jacobs | |
| RE39,321 E | 10/2006 | MacPhee et al. | |
| 2002/0177866 A1 * | 11/2002 | Weikel et al. | 606/192 |
| 2004/0236371 A1 | 11/2004 | McNally-Heintzelman et al. | |
| 2005/0004599 A1 | 1/2005 | McNally-Heintzelman et al. | |
| 2007/0260325 A1 * | 11/2007 | Wenz | 623/23.62 |
| 2007/0269518 A1 * | 11/2007 | Walline et al. | 424/484 |
| 2007/0270974 A1 | 11/2007 | Aeschlimann et al. | |

FOREIGN PATENT DOCUMENTS

| | | | |
|---|---|---|---|
| WO | WO 02/34310 A2 * | 5/2002 | A61L 31/04 |
| WO | WO 02/069817 A | 9/2002 | |
| WO | WO 2008/089172 A | 7/2008 | |
| WO | WO 2009/006313 A | 1/2009 | |

* cited by examiner

APPARATUS AND METHODS OF FIXATING BONE

CROSS-REFERENCE TO RELATED APPLICATION

This is a Divisional Application of U.S. patent application Ser. No. 12/101,571 filed Apr. 11, 2008. The disclosure of the prior application is hereby incorporated by its entirety by reference.

BACKGROUND

The present technology relates to apparatus and methods of treating or repairing hard tissue defects.

The treatment of a hard tissue defect, such as fractured or misshapen bone, involves a number of complex surgical procedures. More effective apparatus and methods are desired to enable such treatment, and to promote and enhance tissue repair in terms of clinical ease of use, cost, healing and efficacy.

SUMMARY

In some aspects, the present technology provides a method of fixating bone comprising connecting at least two bones and a scaffold material with an adhesive component such that the adhesive component is in contact with at least a portion of a surface of each of the bones and the scaffold material. The method further includes fixating the bones and the scaffold material to define a desired structure having a desired rigidity based on changing a material state of the adhesive component.

In another aspect, a method of craniomaxillofacial surgery comprises accessing at least two bones at least partially defining a hard tissue defect at a location within a body, wherein the location comprises a cranial location or a maxillofacial location. The method further includes positioning the bones into a desired relative orientation, conforming a scaffold material to at least a portion of a surface of each of the bones, and contacting an adhesive component between at least a portion of each of the bones and the scaffold material. Additionally, the method includes fixating the bones and the scaffold material in the desired relative orientation to remodel the hard tissue defect. The fixating is based on changing the adhesive component to a material state at which the adhesive component fastens together the bones and the scaffold material with a desired rigidity.

In a further aspect, a composite bone structure comprises a first bone having a first surface and at least one other bone, wherein each other bone comprises a respective second surface. The composite bone structure also includes a scaffold material positioned to connect the first bone and the at least one other bone, wherein the scaffold material is adaptable to conform to the first surface and each respective second surface. Additionally, the composite bone structure includes an adhesive component in contact with at least a portion of the first bone, each other bone and the scaffold material, wherein the adhesive component is changeable to a material state at which the adhesive component affixes the first bone, each other bone and the scaffold material to define a composite bone structure having a desired rigidity.

Further areas of applicability of the present teachings will become apparent from the detailed description provided herein. It should be understood that the detailed description and specific examples, while indicating various embodiments of the technology described below, are intended for purposes of illustration only and are not intended to limit the scope of the teachings.

BRIEF DESCRIPTION OF THE DRAWINGS

The present teachings will become more fully understood from the detailed description and the accompanying drawings, wherein.

DETAILED DESCRIPTION

The following description of technology is merely exemplary of the subject matter, manufacture and use of one or more inventions, and is not intended to limit the scope, application, or uses of any specific invention claimed in this application or in such other applications as may be filed claiming priority to this application, or patents issuing therefrom.

Figure 1:
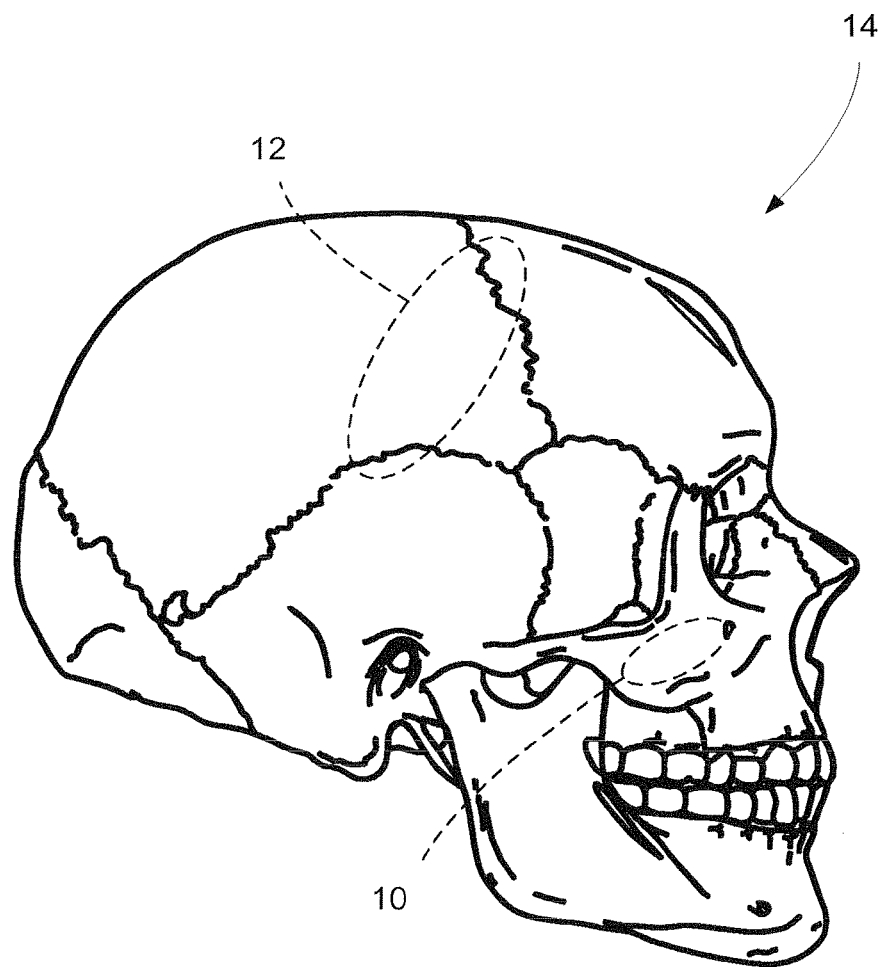
FIG. 1 is a perspective view of representative sites of hard tissue defects subject to treatment or repair according to the technology described herein.

Referring to FIG. 1, the described apparatus and methods of fixating bone relate to therapies or treatments for a hard tissue defect, which includes fractured or misshapen or deficient bone in a body of a patient. The hard tissue defect may be located anywhere on the body, and will be discussed specifically in relation to a maxillofacial defect 10 or a cranial defect 12 on a skull 14 of a patient. For example, the apparatus and methods of fixating bone may include procedures such as, but not limited to: cranial or calvarial vault remodeling; maxillary complex fracture fixation procedures; comminuted bone procedures; cranial or neurosurgical flap procedures; craniosynostosis procedures; infant craniofacial surgery; pediatric reconstructive procedures; pediatric mid-face and craniofacial trauma procedures; brow-lift procedures; bonegraft procedures in the mid-face, mandible or craniofacial skeleton; trauma and reconstructive procedures of the midface or craniofacial skeleton, including frontal, parietal, temporal, sphenoid and occipital bones; fixation of fractures of the maxilla, zygoma, zygomatic arch, orbital rim, frontal sinus wall, nasal, ethmoid and lacrimal bones; iliac crest graft cover; mandibular osteotomies; tumor reconstruction in the mid-face or craniofacial procedures; Lefort fractures (I,II, III); proximal tibia revisions; and generally any bone defect correction procedure. Additionally, as referred to herein, the term "hard tissue" relates to bone, skeletal or ossified tissue, which is relatively hard and rigid as compared to other bodily tissue such as skin.

General Method

Figure 2:
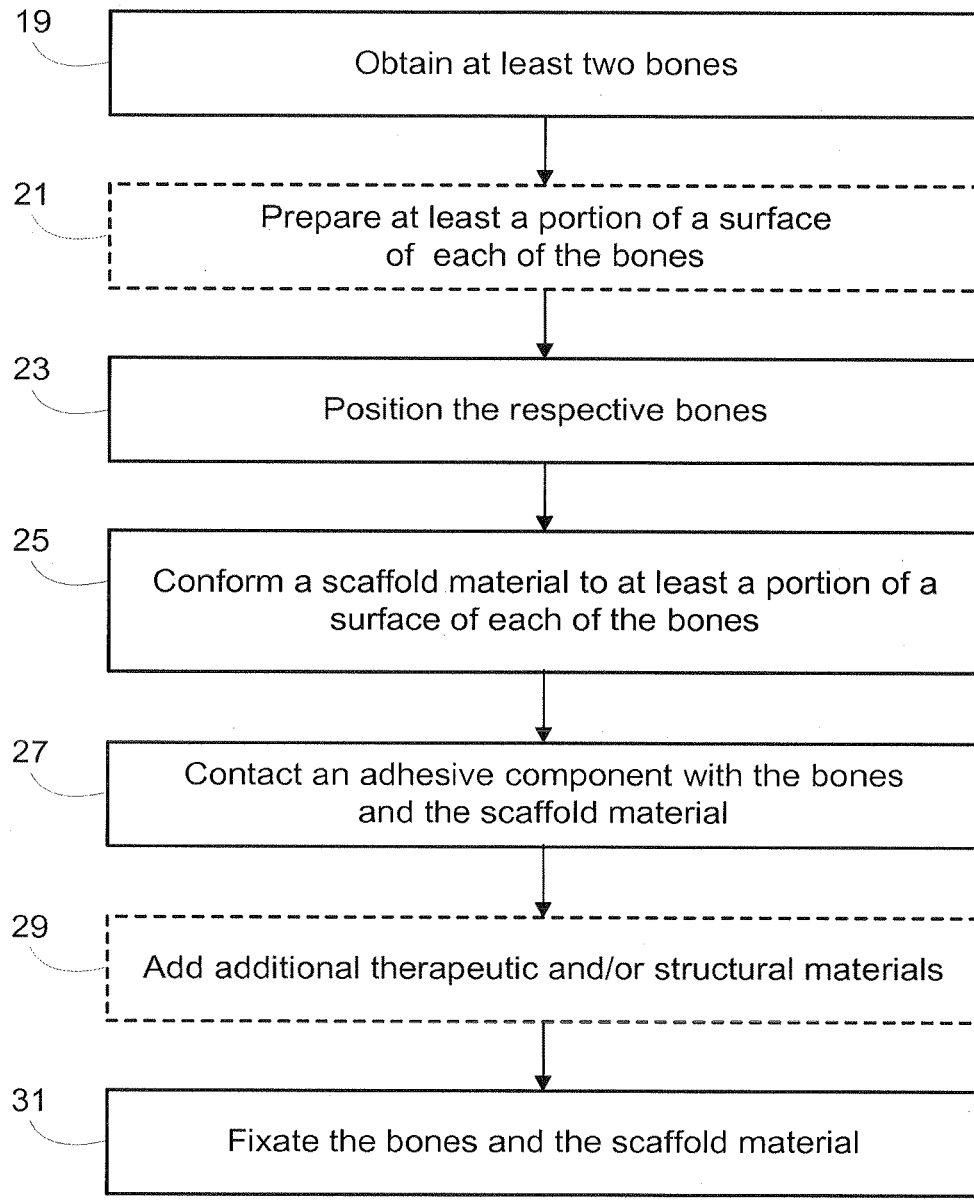
FIG. 2 is a diagrammatic representation of one aspect of a representative method of fixating bone to treat the hard tissue defect of FIG. 1.

Referring to FIG. 2, in one aspect, a method of fixating bone to provide therapy for or treatment of a hard tissue defect includes obtaining two or more bones (Block 19). For example, the bones may be obtained from the site of the hard tissue defect, as the treatment or therapy may involve remodeling the defect into a desired structure. Optionally, as indicated by dashed lines, the method may include preparing at least a portion of a surface of each of the bones (Block 21). The surface preparation is provided to enhance an ability of the bone to be fixated. The method involves positioning the bones for fixation (Block 23) in a desired relative orientation to achieve a desired remodeled structure. Further, the method includes conforming a scaffold material, as defined below, to at least a portion of the surface of each of the bones (Block 25). For example, the scaffold material may be positioned in contact with the respective prepared surfaces. Moreover, the method includes contacting an adhesive component with and between each of the bones and the scaffold material (Block 27). The adhesive component or a portion of the adhesive component may be carried by the scaffold material, or may be added to the construct, or both. Optionally, as indicated by dashed lines, the method may include adding additional therapeutic or structural materials, or both, to the structure (Block 29). For example, bone growth-promoting materials may be added to promote bone fusion, or bone void fillers such as bone cement or bone-growth scaffold may be added to fill in gaps between the bones. Additionally, the method includes fixating the bones and the scaffold material (Block 31) to form a composite hard tissue or bone structure that defines at least a portion of the desired remodeled structure. The fixating includes changing a state of at least the adhesive component, and optionally of the scaffold material, to secure the bones and the scaffold material in the desired relative orientation. Each of the aforementioned actions will be more fully discussed below.

Obtain Bones

As discussed above, at least two bones are obtained (Block 19). For example, in one aspect, referring to FIGS. 1 and 3, the at least two bones 30 and 32 (FIG. 3) may be obtained from a surgical site or location, such as the site of hard tissue defect 10 or 12 (FIG. 1). Further, referring to FIGS. 6 and 7, for example, more than two bones 30, 32 and 33 may include bones associated with a hard tissue defect 11, such as a fracture or multiple fractures in a long bone, in a zygomatic arch, or in any other skeletal structure. Although discussed as being obtained from hard tissue defect 10 or 11 or 12, it should be further understood that in other aspects obtaining bones 30 and 32 (and/or 33) may include obtaining one or more bone segments from other bodily locations, obtaining one or more allograft bone segments, or any combination thereof. Further, although discussed in terms of the at least two bones 30 and 32, it should be understood that the described aspects are not limited thereto, but may include any number of bone segments. Moreover, the two or more bones 30 and 32 may include at least one portion of bone connected to a skeletal structure, or at least one separate bone segment, or both. Additionally, the at least two bones 30 and 32 include hard tissue, which as noted above comprises bone, skeletal and/or ossified tissue. For example, in some aspects, the at least two bones 30 and 32 may be fractured portions of bone, such as may result from local trauma. In other aspects, for example, the at least two bones 30 and 32 may be deformed portions of bone. Further, the term "bone" may include a bone, any part or segment of a bone, or any fragment of a bone.

Additionally, obtaining the at least two bones 30 and 32 may further include a surgical procedure including accessing a harvesting location in the body of the patient. For example, the surgical procedure may include making an incision through the skin and other soft tissue of the patient at the harvesting location to expose one or more of the at least two bones 30 or 32. Further, obtaining the at least two bones 30 or 32 may include removing fractured portions of bone from the accessed location, repositioning fractured portions of bone within the accessed location, cutting the bone at the accessed location to define one or more of the at least two bones 30 or 32, or a combination of both. Alternatively or in addition, as noted above, obtaining the at least two bones 30 or 32 may further include obtaining one or more allograft bone segments.

Prepare Surfaces

Figure 3:
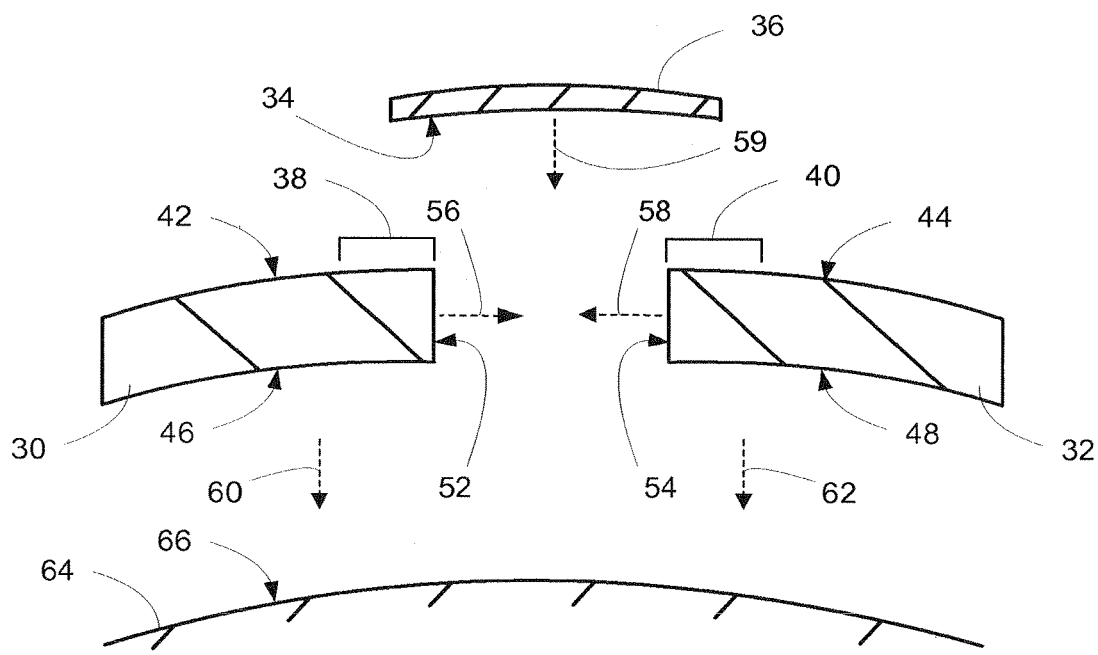
FIG. 3 is an exploded, cross-sectional view of one aspect of representative components of a composite bone implant.
Figure 6:
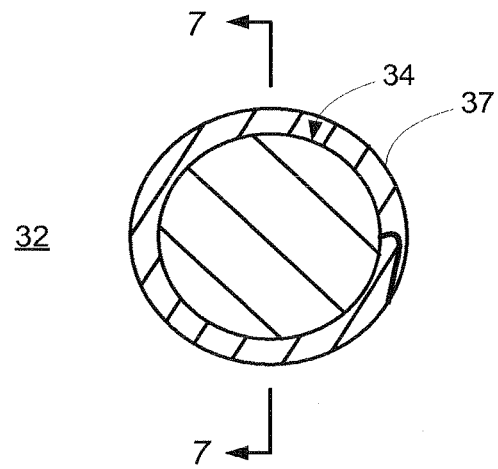
FIG. 6 is a transverse cross-sectional view of another aspect of a composite bone structure.
Figure 7:
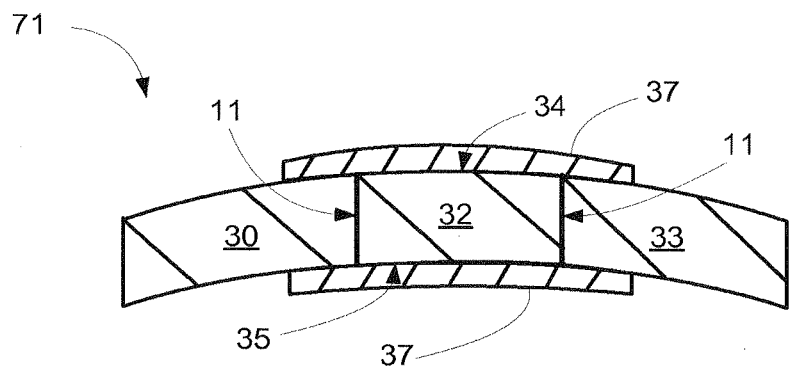
FIG. 7 is a cross-sectional view of the composite bone structure in plane 7-7 of FIG. 6.

Referring again to FIG. 2, the method optionally includes applying a surface preparation to at least a portion of a surface of the bones 30 and 32 (and, optionally, 33) (Block 21). Although the surface preparation (Block 21) is shown in FIG. 2 and discussed herein as occurring prior to the positioning of bones 30 and 32 (Block 23), the surface preparation may be applied at any time before, during or after the positioning. Referring to FIGS. 3, 6 and 7, the surface preparation may include any surface treatment effective to increase an ability of adhesive component 34 to secure scaffolding material 36 or 37 to the respective bones 30 and 32 (and 33), to improve fusion with an adjacent bone segment, to shape the respective bones 30 or 32 (or 33) into a desired form, or any combination thereof. It should be noted that the surface treatment may be applied to any surface used to connect together one or more bones or a bone and the scaffold material.

Referring specifically to FIG. 3, in one aspect, the surface preparation may be applied to at least a respective portion, such as portions 38 and 40, of a respective external or top surface 42 and 44 of the respective bones 30 and 32. It should be noted, however, that internal or bottom surfaces, and/or side surfaces may likewise be treated depending on the particular circumstance or preference of the user. In one aspect, the respective portion 38 and 40 substantially corresponds to an area in which scaffolding material 36 will be placed. The surface preparation may include roughening the top or external-facing surface 42 and 44. In this respect, the top or external-facing surface 42 and 44 faces away from the body of the patient, and opposed to a respective bottom or internal-facing surface 46 and 48. For example, such surface roughening may comprise mechanically abrading the respective bone surfaces, such as with a surgical tool having an abrading element, or may comprise removal of a portion of the surface, such as with a surgical tool having a cutting element. Alternatively, or in addition, the surface preparation may be applied to respective side surfaces 52 and 54, defined between each respective top or external-facing surface 42 and 44 and each respective bottom or internal-facing surface 46 and 48, to improve an ability of the respective side surfaces 52 and 54 to fuse to one another or alter the bonding interface with the adhesive component 34.

Figure 4:
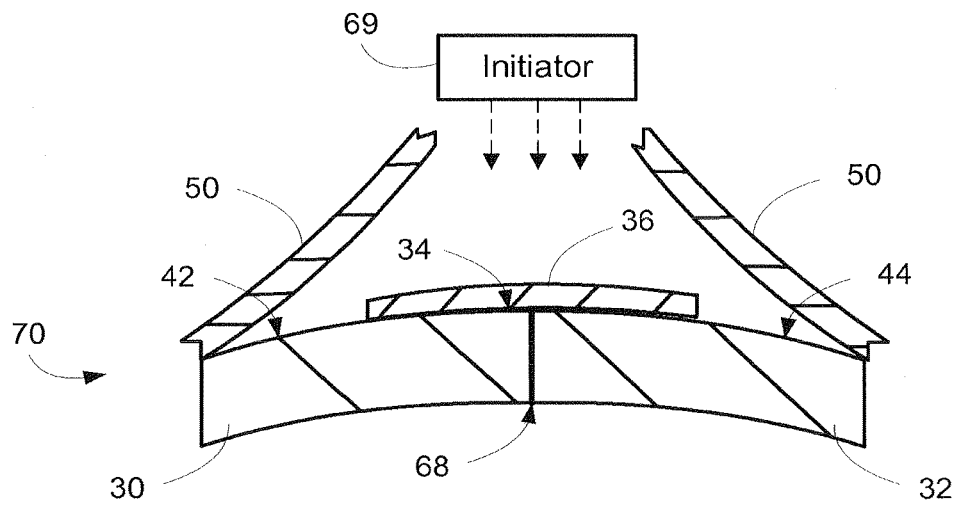
FIG. 4 is a cross-sectional view of the composite bone implant of FIG. 3 forming a desired structure.

Referring to FIG. 4, additionally or alternatively, in other aspects, the surface preparation may include temporarily or permanently removing or peeling back a periosteum layer 50 from the respective portions 38 and 40 of the respective top or external-facing surfaces 42 and 44 of the bones 30 and 32. Further, the surface preparation may include reshaping one or more of bones 30 and 32 to obtain a desired remodeled structure to treat hard tissue defect 10 or 12. Alternatively, or in addition, the surface preparation may further include drying the respective portions 38 and 40 of the surfaces of bones 30 and 32 to enable improved contact with scaffold material 36 and/or adhesive component 34. In yet other aspects, the surface preparation may include applying a chemical to perform one or more actions, such as removing the periosteum layer 50, roughening at least a portion of respective surfaces of bones 30 and 32, reforming the shape of one or more bones 30 and 32, drying the surface, removing a selected material from the surface, such as a lipid, or any combination thereof.

Position Bone Segments

Referring again to FIG. 2, the bones 30 and 32 (and, optionally, 33) are placed in a desired relative position (Block 23). Although the relative positioning of the bones is shown in FIG. 2 and discussed herein as occurring prior to the conforming of the scaffold material (Block 25) and the contacting of the adhesive component (Block 27), the relative positioning may occur once or may occur multiple times before or after other steps of the described methods. In one aspect, for example referring to FIGS. 3 and 4, respective side surfaces 52 and 54 are positioned opposing one another and are moved into a desired orientation adjacent to one another. In particular, as noted by arrows 56 and 58 (FIG. 3), the at least two bones 30 and 32 are moved toward one another until a desired orientation (FIG. 4) of bones 30 and 32 and/or side surfaces 52 and 54 is achieved. In another aspect, for example, the desired orientation may include a position wherein at least portions, and preferably a majority, of respective side surfaces 52 and 54 are contiguous or are in contact with one another so as to enable bone growth between the respective side surfaces 52 and 54. However, gaps may exist or may be desirable between the at least two bones 30 and 32. In some aspects, for example, such gaps may be filled with a bone void filler, such as a bone cement or a bone-growth scaffold.

Further, for example, the desired orientation (FIG. 4) may include the respective top surfaces 42 and 44 having a desired form, such as an arc, a plane, an orientation, or a combination thereof. Further, for example, the desired orientation may correspond to a desired remodeled structure to treat hard tissue defect 10 or 12. It should be noted that the positioning of the at least two bones 30 and 32 may include positioning in situ, in vitro, or a combination thereof. Additionally, for example referring to FIG. 7, the desired orientation may remodel the long bone, zygomatic arch, or multiple fracture defect into a shape that approximates a non-defective skeletal structure.

In an optional aspect, referring to FIG. 3, as indicated by arrows 60 and 62, the positioning of bones 30 and 32 may include positioning against a mold 64 having a mold surface 66 with a desired shape. For example, the desired shape corresponds to a desired orientation of bones 30 and 32, or a desired remodeled structure to treat hard tissue defect 10 or 12. Although illustrated as positioning bottom or internal-facing surfaces 46 and 48 of bones 30 and 32 against mold surface 66, it should be understood that the optional positioning against mold 64 may alternatively include positioning top or external-facing surfaces 42 and 44 against mold surface 66.

Conform Scaffold

Referring back to FIG. 2, the method further includes conforming the scaffold material, which in some optional aspects may include the adhesive component, to at least a portion of the surface of each of the bones (Block 25). In one aspect, for example referring to FIGS. 3 and 4, scaffold material 36 is moved in direction 59 and placed across an interface or gap 68 (FIG. 4) between the opposing side surfaces 52 and 54 of bones 30 and 32. In particular, in one aspect, at least a part of scaffold material 36 is placed into contact with the opposing prepared surface portions 38 and 40 of bones 30 and 32, thereby bridging interface 68. Although illustrated as a plane, it should be noted that interface 68 may comprise any shape or combination of shapes. Further, for example, scaffold material 36 is positioned such that at least a portion of adhesive component 34 connects between scaffold material 36 and the opposing prepared surface portions 38 and 40 of bones 30 and 32. As such, scaffold material 36, which may include or carry adhesive component 34, is positioned in a manner to allow for securing bones 30 and 32 (and, optionally, 33 in FIG. 7) in a desired relative orientation, and to further bridge interface 68 (or defect 11 in FIG. 7) to promote bony fusion between the adjacent bone segments.

In another aspect, referring to FIGS. 6 and 7, scaffold material 37 may be wrapped around hard tissue defect 11, thereby fully enveloping the defective skeletal structure. In this aspect, the wrapping of the scaffold material 37 and subsequent fixation provides support to the structure in multiple directions.

Scaffold material 36 (or 37) may comprise any material capable of carrying adhesive component 34. For example, scaffold material 36 (or 37) may include, but is not limited to, materials such as a woven fabric, a mesh, a foam, a plate, a perforated membrane, a sheet, a porous structure, a PolyLactide weave or any combination thereof. Further, for example, scaffold material 36 (or 37) may have a surface that includes voids, peaks and valleys, ridges, grooves, channels, any combination thereof, or any other irregular surface that improves an ability of adhesive component 34 to bond or interdigitate with scaffold material 36 (or 37). Further, for example, scaffold material 36 (or 37) may be pre-impregnated with a desired or an effective amount of adhesive component 34, or all or some portion of the desired or effective amount of adhesive component 34 may be added to scaffold material 36 (or 37) at any time during the procedure described herein. For example, the desired or effective amount of adhesive component may comprise an amount effective to enable binding between scaffold material 36 (or 37) and at least respective portions 38 and 40 of respective bones 30 and 32, or to provide a desired rigidity or stiffness to the resulting structure, or both. Additionally, scaffold material 36 (or 37) may be sized so that the combination of bone segments 30 and 32 and scaffold material 36 (or 37) define a desired remodeled structure.

Further, scaffold material 36 (or 37) comprises a biocompatible material. In some aspects, scaffold material 36 (or 37) further comprises a bioresorbable material. For example, scaffold material 36 (or 37) may comprise a polymer, a resorbable polymer, a urethane, a polyeurethane, a metal, a biocompatible material, a calcium salt material, a tissue, collagen, cellulose or combinations thereof. In one example, which is not to be construed as limiting, scaffold material 36 (or 37) may comprise a LACTOSORB plate available from Biomet, Inc. of Warsaw, Ind.

Contact the Adhesive with Bones and Scaffold

Referring back to FIG. 2, the method further includes contacting the adhesive component between the bones and the scaffold material (Block 27). As previously noted, adhesive component 34 may be carried by scaffold material 36 or 37, or may be separately added, or both. In one aspect, for example, scaffold material 36 or 37 includes adhesive component 34 on a surface facing the bones 30 and 32 (and, optionally, 33), thereby connecting the bones and the scaffold material when the scaffold material is adapted to conform to at least a portion of the respective surfaces of the bones.

Additionally, adhesive component 34 may comprise any material capable of forming a bond between scaffold material 36 or 37 and bones 30 and 32 (and, optionally, 33), whether by chemical bonding, interdigitation or another method or combination of methods used to form a mechanical bond between the scaffold material and bone segments. Further, adhesive component 34 comprises a biocompatible material. In some aspects, adhesive component 34 further comprises a bioresorbable material. For example, adhesive component 34 may comprise a material such as a polymer, a urethane, a polyeurethane, an amino acid containing polymer, an acrylic, a cyanoacrylate, a polymethyl methacrylate (PMMA), an alkylene bis(oligolactoyl) methacrylate, a fibrin-based material, a bone welding material, or combinations thereof.

In one example, which is not to be construed as limiting, adhesive component 34 may comprise a synthetic polymer, such as a biodegradable, polyester urethane/urea composition. For example, adhesive component 34 may comprise a combination of pre-polymers operable to react to form a cross-linked polymer network. For example, the combination of pre-polymers may include a first pre-polymer having isocyanate groups, such as from the combination of lysine diisocyante and pentaerythritol, and a second pre-polymer comprising a multi-branched polyol, such as poly(lactic acid) polyol (PLA), polyglycolic acid (PGA), caprolactone, etc. For example, the biodegradable, polyester urethane/urea composition may comprise one of the NOVOSORB materials available from PolyNovo Biomaterials Pty. Ltd. of Australia.

Additionally, in some aspects, adhesive component 34 comprises a plurality of states, including an initial unpolymerized or minimally polymerized state prior to and upon positioning of scaffolding material 36 (or 37) and bones 30 and 32 (and 33), then a fully polymerized or cured state after such positioning, for example, after exposure to an initiator 69 such as an additional chemical component, a light or radiation wave, etc., as will be discussed below in more detail.

Additionally, in some aspects, scaffold material 36 (or 37) and adhesive component 34 may be formed from substantially the same material. Alternatively or in addition, in some aspects where both are bioresorbable, scaffold material 36 (or 37) and adhesive component 34 may be formed from materials having substantially the same rate of resorption, which may provide a therapeutic benefit with respect to uniform degradation of the fixated structure, avoiding inflammation, or providing improved healing.

Add Additional Materials

Referring to FIG. 2, the method may optionally include adding additional therapeutic or structural materials, or both, to the structure (Block 29). For example, bone growth-promoting materials may be added to promote bone fusion. Further, for example, void fillers such as bone cement or bone-growth scaffold may be added to fill gaps between the bones. Additionally, other therapeutic agents such as gene therapy agents, infection-avoidance agents, pain-relieving agents, etc., may be added.

Fixate Bone Segments

As discussed above, and referring again to FIGS. 2, 4 and 7, once the bone segments and scaffold material are positioned as desired and contacted with the adhesive component, the bones and scaffold material are fixated relative to one another to form a composite bone structure (Block 31). In one aspect, for example, fixating bones 30 and 32 (or 30, 32 and 33) is based on changing at least adhesive component 34 from a first material state to a second material state. At the first material state, adhesive component 34 may comprise a relatively flexible state. For example, in some aspects, the first material state may be a liquid state, a semi-solid state, or a non-rigid solid state. In some aspects, for example, the first material state has a viscosity sufficient to enable adhesive component 34 to be controllably positioned. For example, adhesive component 34 may be controllably positioned by having a viscosity and adhesion characteristic that allows adhesive component 34 to be controllably maintained on a desired surface, such as on a respective bone surface or on scaffold material, or both, to allow a user to avoid contacting the adhesive component with non-desired contact areas, such as areas within a surgical site other than the prepared surfaces of the bones or other than within scaffold material, or both. In any case, at the first material state, adhesive component 34 comprises sufficient flexibility to enable contact with bones and scaffold material. At the second material state, adhesive component 34 is operable to bind to scaffold material 36 as well as to two or more bones 30 and 32 (or 30, 32 and 33). Further, at the second material state, adhesive component 34 forms a structure having a desired rigidity or stiffness. The desired rigidity or stiffness may include, but is not limited to, a range of rigidities or stiffnesses substantially corresponding to the range of rigidities of hard tissue, such as the particular hard tissue comprising one or more of bones 30 and 32 (or 30, 32 and 33). In any case, at the second material state, adhesive component 34 comprises sufficient rigidity or stiffness to resist movement of the bones and scaffold material from the desired shape or orientation. For example, the amount of such resistance may be based on typical skeletal loads at the given defect location, or on the typical strength of bones in the defect location, or both. Thus, referring to FIGS. 4, 5 and 7, adhesive component 34, which may be carried by scaffolding material 36 or 37, changes into a state to secure scaffold material 36 (or 37) and two or more bones 30 and 32 (or 30, 32 and 33) at a desired orientation, thereby forming a composite bone structure 70 (FIG. 5) or 71 (FIG. 7) having a desired shape or form to treat or remodel hard tissue defect 10 or 12 (FIG. 1) or 11 (FIG. 7).

Optionally, in some aspects, the fixating may further include changing the state of scaffold material 36 (or 37) from a first state having substantial flexibility to a second state having substantial rigidity or stiffness. For example, the substantial flexibility comprises an amount of flexibility that allows scaffold material 36 or 37 to conform to a surface of the two or more bones 30 and 32 (or 30, 32 and 33). Further, for example, the substantial rigidity may include an amount of rigidity or stiffness at the second state greater than the amount that existed at the first state, which may include an amount of rigidity or stiffness to resist movement of the bones and the scaffold material out of the desired shape or form.

In particular, referring specifically to FIG. 4, in aspects in which adhesive component 34, and optionally scaffold material 36 (or 37), comprises a polymer, the changing of states of adhesive component 34 involves application of an initiator 69 operable to change at least adhesive component 34 to a second polymer state different from a first polymer state, wherein the second polymer state comprises a cured state or a partially-cured or partial polymerization state. For example, depending on the specific procedure, it may be desirable to fully cure adhesive component 34 at one time, hence fully setting the form and structure of the resulting composite bone structure 70 (or 71; FIG. 7). In other aspects, for example, it may be desirable to only partially cure adhesive component 34, allowing for later manipulation of the form or structure of composite bone structure 70 or 71. For example, the partial polymerization state is some state achieving less than substantially all of the mechanical strength of the adhesive, where mechanical strength may include one or more of bonding strength, rigidity, or stiffness. In such a case, once composite bone structure 70 or 71 has been completely positioned, then the method may include changing from the second state of partial polymerization to a third state of substantially full polymerization or full cure, thereby securing the relative orientation of composite bone structure 70 or 71.

As noted above, the state changes may be effected by initiator 69. Initiator 69 may include, but is not limited to, a radiation-based initiator, of which a light based initiator would be one example, a temperature change-based initiator, a chemical-based initiator, or any combination thereof or any combination of different types of each one. For example, adhesive component 34 may comprise a multi-part adhesive having at least two parts, wherein combination of a second part with the first part initiates a chemical reaction operable to change adhesive component 34 from the first relatively flexible state to the second relatively rigid state. One example of such a multi-part adhesive component 34 includes, but is not limited to, a biodegradable, polyester urethane/urea composition such as one of the NOVOSORB materials available from PolyNovo Biomaterials Pty, Ltd. of Australia. In another example, the radiation-based, or more specifically the light-based, initiator may comprise exposure to one or more light waves or radiation waves having a desired wavelength or range/band or ranges/bands of desired wavelengths to effect curing of the adhesive component. For instance, with adhesive component 34 comprising a urethane-based polymer, the initiator 69 may comprise ambient light, which includes as a component light of the wavelength of interest and which may slowly cure the adhesive component. However, a light of greater intensity and, specifically, with a greater intensity at a specific wavelength or band of wavelengths may be used to accelerate the light based curing process.

As noted above, the application of initiator 69 may differ throughout the fixation process, such as in the case where a partial fixation is achieved prior to a final fixation. For example, in the case of adhesive component 34 comprising a polymer, the method of causing polymerization up to a partial polymerization state may further include exposing adhesive component 34 to a first radiation at a first set of one or more wavelengths for a first time period operable to achieve less than substantially all of the mechanical strength of adhesive component. In this aspect, in one example, the first radiation has a source including a laser or other directed source that generates locally-focused radiation waves directed substantially on adhesive material 34. In this case, in one optional aspect, changing adhesive component 34 to the substantially fully polymerized state may include additionally exposing adhesive component 34 to the first radiation for a second time period. In a different optional aspect, changing the adhesive component to the substantially fully polymerized state may include additionally exposing the adhesive component to a second radiation for a second time period and/or at a second set of one or more wavelengths different from the first set of one or more wavelengths. For example, the second radiation may have a source including a different type of laser or other directed light source, or may include an ambient radiation source operable to generate non-locally-focused light waves, i.e. radiation or light waves not directed primarily on the adhesive component or the scaffold material.

Optionally, in some aspects, adhesive component 34 (and/or scaffold material 36 or 37) may have a different perceived color at each material state. Thus, by changing from one perceived color to another, which includes a shift in wavelength (for example, from red to blue) or a shift in intensity (for example, from light blue to dark blue), adhesive component 34 may provide a perceptible visual indicator corresponding to the respective material state, thereby aiding a surgeon or other party in ascertaining the material state.

As noted above, although composite bone structure 70 or 71 has been discussed in terms of bones 30 and 32 or 30, 32 and 33, any number of bones may be utilized. Similarly, one or more composite bone structures 70 or 71 may be joined together, or composite bone structure 70 or 71 and non-harvested bone, such as adjacent to the site of hard tissue defect 10, 11 or 12, may be joined together in a similar manner as described above for joining two or more bones 30 and 32, or 30, 32 and 33.

For example, the method of joining composite bone structure to another bone may include positioning the composite bone structure adjacent to at least one other bone at the implant site. Further, the method may include positioning a second scaffold material including a second adhesive component across at least a portion of each of the composite bone structure and the at least one other bone such that the second adhesive component is in contact with both the composite bone structure and the at least one other bone. When performing the conforming and the contacting, the second scaffold material and the second adhesive component both comprise a material state being substantially flexible. Finally, this method includes fixating the composite bone structure and the at least one other bone based on changing at least the second adhesive component to another material state at which the second adhesive component chemically or mechanically binds to the second scaffold material, the composite bone structure and the at least one other bone, thereby forming a structure having a desired rigidity, as described above.

Figure 5:
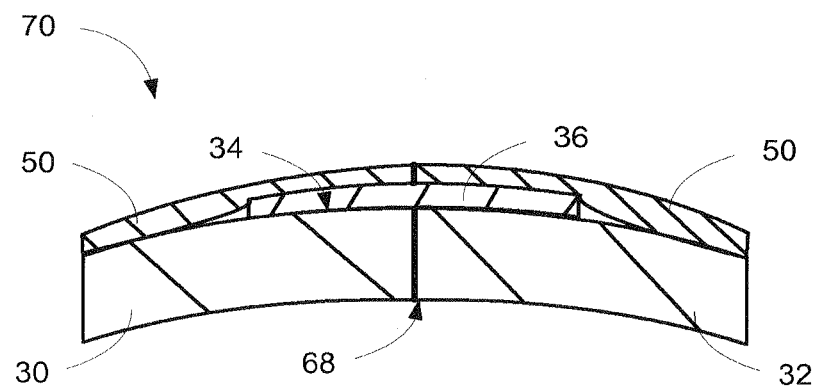
FIG. 5 is a cross-sectional view of the composite bone implant of FIG. 3 in a final state.

Additionally, it should be noted that although FIGS. 4 and 5 include bone segments 30 and 32 having periosteum 50, one or both of bone segments 30 and 32 may be obtained without periosteum 50, such as in the case of one or both segments 30 and 32 comprising allograft bone or as in the case where the periosteum is removed from the patient's own bone intraoperatively.

In another example, in some aspects, the method of FIG. 2 may be utilized specifically for craniomaxillofacial surgery. In this case, for example, the method of craniomaxillofacial surgery includes accessing at least two bones at least partially defining a hard tissue defect at a location within a body, wherein the location comprises a cranial location or a maxillofacial location or mandible. In this case, at least one of the bones may be obtained from the defect location, while one or more of the other bones may be obtained from another harvesting location on the body, or may be obtained as an allograft. In other cases, such as when a reconstruction is desired using the existing hard tissue, the bones may be obtained from the hard tissue location. Further, it should be noted that at least one of the bones may be a portion of cranial or maxillofacial bone at or adjacent to the hard tissue defect location and connected to or integral with the skull. Additionally, in this specific example, the hard tissue defect location comprises one of a cranial location or a maxillofacial location.

Further, the method of craniomaxillofacial surgery includes positioning the bones into a desired relative orientation. Generally, the bones are positioned such that opposing surfaces of the respective bone segments are facing one another, thereby defining an interface between the bone segments.

Additionally, the method of craniomaxillofacial surgery includes conforming a scaffold material to at least a portion of a surface of each of the bones. Further, the method includes contacting an adhesive component between at least a portion of each of the bones and the scaffold material. In this case, for example, the scaffold material spans the interface between the bones, thereby allowing the adhesive component to define a connection between the bones and the scaffold material. Additionally, to enable achieving a desired contact between the scaffold material and adhesive component and the bones, the scaffold material and the adhesive component both comprise a first material state being substantially flexible to allow such contact.

Additionally, the method of craniomaxillofacial surgery includes fixating the bones and the scaffold material in the desired relative orientation to remodel the hard tissue defect.

In this case, the fixating is based on changing at least the adhesive component to a second material state at which the adhesive component mechanically or chemically binds the bones and the scaffold material, thereby forming a composite bone structure having a desired rigidity. In an optional aspect, the fixating may involve both the adhesive component and the scaffold material changing into the second material state to define the relatively rigid structure used to repair the hard tissue defect.

Thus, referring again to FIGS. 3-5 and 7, the above-described methods allow for the formation of a composite bone structure 70 (FIG. 5) or 71 (FIG. 7) that includes hard tissues/bones 30 and 32, or 30, 32 and 33, joined together by an adhesive component 34 carried by a scaffold material 36 or 37. For example, referring to FIGS. 3-5, hard tissue/bone 30 has a first surface 52 and hard tissue/bone 32 has a second surface 54, and bones 30 and 32 are relatively positioned so as to define an interface 68 between at least a portion of the respective surfaces 52 and 54. Further, scaffold material 36 is positioned adjacent to at least a portion of the hard tissues/bones 30 and 32, such that scaffold material 36 spans at least a portion of interface 68. Further, adhesive component 34 is in contact with at least a portion of each of the hard tissues/bones 30 and 32 and scaffold material 36. Scaffold material 36 and adhesive component 34 both initially comprise a first material state being substantially flexible to enable their positioning relative to the respective hard tissues/bones 30 and 32. After achieving the desired positioning, at least adhesive component 34 is changeable to a second material state at which adhesive component 34 binds to each of the hard tissues/bones 30 and 32 and scaffold material 36, thereby defining composite bone structure 70 having a desired rigidity. Similarly, with respect to FIG. 7, scaffold material 37 wraps around hard tissues/bones 30, 32 and 33, and adhesive component 34 affixes the hard tissues/bones 30, 32 and 33 and scaffold material 37 in a desired orientation and further defines composite bone structure 71 having a desired rigidity.

While the foregoing disclosure discusses illustrative aspects and/or embodiments, it should be noted that various changes and modifications could be made herein without departing from the scope of the invention as defined by the appended claims. Furthermore, although elements of the described aspects and/or embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise.

What is claimed is:

1. A method of fixating bone, comprising:
   holding at least two bones in a relative orientation;
   connecting the bones and a scaffold material by applying an adhesive component only on a surface of each of the bones and the scaffold material, including conforming the scaffold material to at least a portion of the surface of each of the bones and fully enveloping the bones with the scaffold material while positioned in the relative orientation; and
   fixating the bones and the scaffold material to define a structure having fixed dimensions and a rigidity based on changing the material state of the adhesive component and the material state of the scaffold material, including changing the material state of the adhesive component and changing the material state of the scaffold material after the conforming and while the bones are positioned in the relative orientation.

2. The method of claim 1, wherein the adhesive component comprises a synthetic polymer, and wherein the fixating further comprises exposing the adhesive component to a radiation-based initiator or a chemical-based initiator operable to change the adhesive component to a cured state.

3. The method of claim 1, wherein the adhesive component comprises a synthetic polymer, and wherein the fixating further comprises polymerizing the adhesive component to a partial polymerization state, repositioning at least one of the bones while connected to the adhesive component in the partial polymerization state, and allowing or actively promoting further polymerizing of the adhesive component from the partial polymerization state to a substantially full polymerization state to fixate the repositioned bones and the scaffold material.

4. The method of claim 3, wherein changing the adhesive component to the substantially full polymerization state further comprises exposing the adhesive component to an ambient radiation source not directed primarily on the adhesive component or the scaffold material.

5. The method of claim 1, wherein applying the adhesive component further comprises applying on an external portion of the surface of each of the bones.

6. The method of claim 1, wherein an amount of rigidity of the of the scaffold material after changing the material state of the scaffold material is greater than an amount of rigidity of the scaffold material prior to changing the material state of the scaffold material.

7. A method of fixating bone, comprising:
   connecting at least two bones and a scaffold material by applying an adhesive component only on a surface of each of the bones and the scaffold material, wherein the adhesive component comprises a synthetic polymer; and
   fixating the bones and the scaffold material to define a structure having a rigidity based on changing a material state of the adhesive component, wherein the fixating further includes:
   polymerizing the adhesive component to a partial polymerization state;
   repositioning at least one of the bones while connected to the adhesive component in the partial polymerization state; and
   allowing or actively promoting further polymerizing of the adhesive component from the partial polymerization state to a substantially full polymerization state to fixate the repositioned bones and the scaffold material; and
   wherein changing the adhesive component to the substantially full polymerization state further comprises exposing the adhesive component to an ambient radiation source not directed primarily on the adhesive component or the scaffold material.

8. The method of claim 7, wherein the rigidity substantially corresponds to a rigidity of the bones.

9. The method of claim 7, wherein changing the material state of the adhesive component further comprises changing the adhesive component from a first perceived color to a second perceived color, wherein the second perceived color is perceptively different from the first perceived color.

10. The method of claim 7, wherein the scaffold material comprises a first biocompatible material and the adhesive component comprises a second biocompatible material, wherein the first biocompatible material and the second biocompatible material have substantially the same rates of resorption.

11. The method of claim 7, wherein the scaffold material and the adhesive component both comprise substantially the same biocompatible material.

12. The method of claim 7, wherein the adhesive component comprises at least one material selected from the group comprising: urethane-based, resorbable synthetic polymer and isocyanate-based, resorbable synthetic polymer.

13. The method of claim 7, in which the bones are obtained from at least one location selected from the group comprising: a cranial skeleton location and a maxillofacial skeleton location.

14. The method of claim 7, further comprising adding the adhesive component to the scaffold material.

15. The method of claim 7, further comprising holding the bones in a relative orientation against a surface of a mold.

16. The method of claim 7, further comprising:
accessing the bones at a location within a body;
removing the bones from the body;
holding of the bones in a relative orientation outside of the body;
wherein the changing of the material state of the adhesive component comprises changing outside of the body; and
securing the fixated bones and scaffold material to at least a portion of a skeletal bone at the location within the body.

17. The method of claim 7, further comprising performing a surface preparation on at least a portion of the surface of each of the bones, wherein the surface preparation improves an ability of the adhesive component to attach to the respective portion of the surface.

18. The method of claim 17, wherein performing the surface preparation further comprises roughening the portion of the surface of each of the bones, and wherein connecting further comprises placing the scaffold material such that the adhesive component contacts the respective roughened surfaces.

19. The method of claim 17, wherein performing the surface preparation further comprises removing at least a portion of periosteum from at least the portion of the surface of each of the bones prior to the connecting with the scaffold material.

20. The method of claim 19, further comprising replacing the portion of the periosteum over the scaffold material at each portion of the surface of the bones after connecting the bones with the scaffold material.

21. The method of claim 7, further comprising adding a bone void filler between at least a portion of the bones.

22. The method of claim 7, further comprising adding a bone growth-promoting material in contact with the bones.

23. A method of fixating bone, comprising:
holding at least two bones in a relative orientation;
connecting the bones and a scaffold material by applying an adhesive component only on a surface of each of the bones and the scaffold material, including conforming the scaffold material to at least a portion of the surface of each of the bones while positioned in the relative orientation; and
fixating the bones and the scaffold material to define a structure having a rigidity based on changing the material state of the adhesive component and the material state of the scaffold material, including changing the material state of the adhesive component and changing the material state of the scaffold material after the conforming and while the bones are positioned in the relative orientation,
wherein the scaffold material comprises a first biocompatible material and the adhesive component comprises a second biocompatible material, wherein the first biocompatible material and the second biocompatible material have substantially the same rates of resorption.

* * * * *